United States Patent

Hägglund

[11] Patent Number: 4,696,780
[45] Date of Patent: Sep. 29, 1987

[54] METHOD OF MANUFACTURING A PROSTHESIS CUFF TO RECEIVE AN AMPUTATION STUMP

[75] Inventor: Lars Hägglund, Veberöd, Sweden

[73] Assignee: Landstingens Inkopscentral LIC, Sweden

[21] Appl. No.: 682,166

[22] Filed: Dec. 17, 1984

[30] Foreign Application Priority Data

Dec. 21, 1983 [SE] Sweden .............................. 83070763

[51] Int. Cl.⁴ ...................... B29C 45/14; B29C 61/02; B29C 65/66
[52] U.S. Cl. .................................. 264/222; 264/227; 264/230; 264/DIG. 30; 264/DIG. 71; 623/33
[58] Field of Search ............... 264/230, 222, DIG. 71, 264/227, DIG. 30; 623/33

[56] References Cited

U.S. PATENT DOCUMENTS

| Re. 25,624 | 7/1964 | Stahl | 264/230 |
|---|---|---|---|
| 1,998,356 | 4/1935 | Brown | 264/230 X |
| 2,424,278 | 7/1947 | Kunkel | 264/222 |
| 3,377,416 | 4/1968 | Kandel | 264/222 |
| 3,393,407 | 7/1968 | Kandel | 264/222 X |
| 3,662,094 | 5/1972 | Wetmore et al. | 264/230 X |
| 3,861,972 | 1/1975 | Glover et al. | 264/DIG. 71 |
| 3,962,395 | 6/1976 | Hägglund | 264/222 X |
| 4,307,056 | 12/1981 | Meyer | 264/222 |
| 4,356,046 | 10/1982 | Yamazaki et al. | 264/230 X |
| 4,473,421 | 9/1984 | Gustafsson | 264/296 X |

FOREIGN PATENT DOCUMENTS 57-115323  7/1982  Japan .................................. 264/230

Primary Examiner—Philp Anderson
Attorney, Agent, or Firm—Ostrolenk, Faber, Gerb & Soffen

[57] ABSTRACT

In a method of manufacturing a prosthesis cuff to receive an amputation stump, particularly for a lower-leg prosthesis, a positive cast of the stump is positioned in an expanded and heat shrinkable rough cuff of a plastics material, whereupon the rough cuff is caused by heating and vacuum-forming to adjust to the surface contour of the stump. The positive cast is subsequently removed. A connecting element for the prosthesis is provided on the rough cuff, for example having formation embedded in the plastics material.

16 Claims, 2 Drawing Figures

METHOD OF MANUFACTURING A PROSTHESIS CUFF TO RECEIVE AN AMPUTATION STUMP

BACKGROUND OF THE INVENTION

The present invention relates to a method of manufacturing a prosthesis cuff to receive an amputation stump, for example for a lower-leg prosthesis, and to a rough cuff for use in performing the method. The invention also relates to a prosthesis cuff manufactured by the method.

There is an acute need in the field of orthopedics for an efficient method of manufacturing individually fitted prostheses. Methods employed hitherto are still mainly manual, especially in the case of prosthesis cuffs intended for amputation stumps for example for lower-leg prostheses It is well known that certain plastics have thermoplastic memory properties, so that for exmaple, if such a plastics material is stretched under certain conditions it will retain its stretched condition until heated to a particular temperature, whereupon it will shrink towards its original form unless physically restrained from doing so. The use of heat-shrinkable rough cuffs having such thermoplastic memory properties has been proposed for the manufacture of the type of prosthesis cuffs under discussion here. According to such prior proposals, such a prefabricated pre-stretched cuff is applied directly around the amputation stump in question and is externally heated to achieve the required fit of the cuff to the outer contour of the amputation stump.

However, in practice it has proved impossible by the proposed methods to achieve the extremely careful fit required between cuff and amputation stump. Thus, for example, in the case of a leg prosthesis, to be able to withstand the considerable forces arising during walking movement of the patient, without damage to the stump, certain delicate points must take up more of the load. This cannot, hwoever, be achieved with the cuffs produced in accordance with such prior proposals, which frequently had a poor fit leading to chafing and pressure sores. It was also found that the shrinkage properties and strength properties together were so limited in such plastic cuffs that any practical use of such directly shrinkable cuffs was unthinkable.

According to established design principles for rough cuffs of this type for leg prostheses, a stump of large diameter generally indicates a heavy, sturdily-built person and the appropriate plastic cuff should therefore be made relatively stronger by making the wall thickness of the cuff relatively thick. Correspondingly, for a stump of lesser diameter, the cuff wall should be made thinner since it may be assumed that such a stump belongs to a slimmer and thus a lighter person. The diameter of an adult person's stump varies by a factor of approximately two and variations in the weight of an adult person are also of this magnitude. This would mean that a cuff of the largest diameter should be designed with a wall thickness approximately twice that of a cuff of the smallest diameter.

If only the shrinkage properties of the plastic are to be utilised, it is found if one starts with a standard rough cuff of given diameter and wall thickness and allows such cuffs to shape themselves to the respective prosthesis stumps by shrinkage, the wall thickness of the finished cuffs will increase as the diameter decreases. This is exactly contrary to the design principles set out above. In order to embrace the above variations in stump sizes by a reasonable margin, a considerable number of standard cuffs is required, with correspondingly large costs for tool-making and stocking.

Attempts have also been made earlier to use a conventional plaster positive of the acutal amputation stump and to perform the final shaping of the cuff around the plaster positive instead of applying prefabricated rough cuffs directly on the amputation stump. This procedure has also proved unsuccessful in practice since the wall material of the cuff is unable during the shrinkage process to follow recesses, hollows and extra load-absorbing depressions normally occurring in the outer surface of the plaster positive. The result is a poor fit, which also gives rise to the drawbacks mentioned above, chafing and pressure sores for the patient.

Finally endeavours have also been made to give the rough cuff its final shape solely by vacuum shaping the cuff around a plaster positive. However, in this process folds occur during the vacuum shaping due to too much excess material in the large cuffs. It will be understood that folds and edges in a prosthesis cuff can in no way be tolerated by the stump for which the cuff is intended.

SUMMARY OF THE INVENTION

An object of the present invention is to eliminate the above drawbacks associated with methods known hitherto and to provide a method of manufacture which, utilising a prefabricated and correctly dimensioned heat shrinkable rough cuff, is able for the first time to produce a prosthesis cuff with an extremely accurate fit to the amputation stump for which it is intended.

According to the invention, there is provided a method of manufacturing a prosthesis cuff to receive an amputation stump, wherein, (a) a cuff-shaped starting product, open at one end, is manufactured from a plastics material having thermoplastic memory, (b) said cuff-shaped starting product is then expanded by at least 25% of its original diameter to form a rough prosthesis cuff, (c) a positive cast of an amputation stump is then inserted and positioned in said rough cuff, and thereafter, (d) the rough cuff with the positive cast thus positioned therein is subjected to heat, to bring the plastics material to its shrinkage temperature so that the rough cuff shrinks around the positive cast and is thus shaped to correspond with the surface contour of the cast, final adjustment of the shape of the cuff to the surface contour of the positive cast, in the final stage of the shrinking process, being effected by the creation of a vacuum in the space between the outer surface of the cast and the inner surface of the rough cuff, and (e) after cooling of the cuff, the cast is removed therefrom.

In a method according to the invention, an optimisation of the measures utilised so far is achieved and this optimisation for the first time permits, without time-consuming work carried out manually, the accurate fitting of a prefabricated rough cuff to a positive of an actual amputation stump.

Preferably an adapter for connection with a prosthesis part is provided at the closed end of the rough cuff at the time of manufacture and this adapter is utilised as a positioning point during the shrinking process. By carrying out also equivalent positioning of the positive cast utilising a position indicator in the positive cast, the positive cast can be positioned in the most suitable manner in the cuff prior to shrinkage, which also greatly contributes to a completely controlled shrinking process.

BRIEF DESCRIPTION OF THE DRAWINGS

An embodiment of the invention is described below with reference to the accompanying drawings.

In the drawings.

DESCRIPTION OF THE PREFERRED EMBODIMENT

Figure 1:
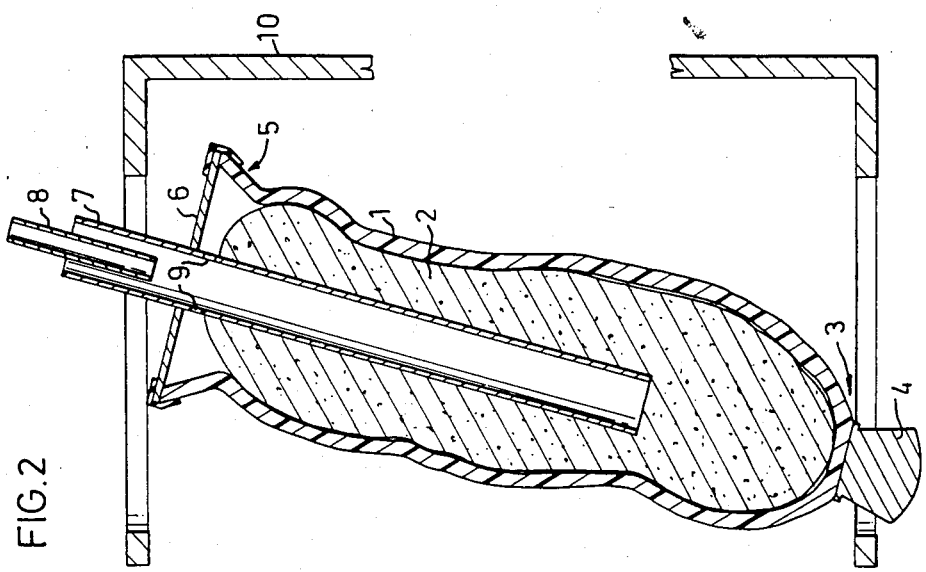
FIG. 1 is a view in section through a rough prosthesis cuff and positive cast prior to shaping the cuff to the positive cast.
Figure 2:
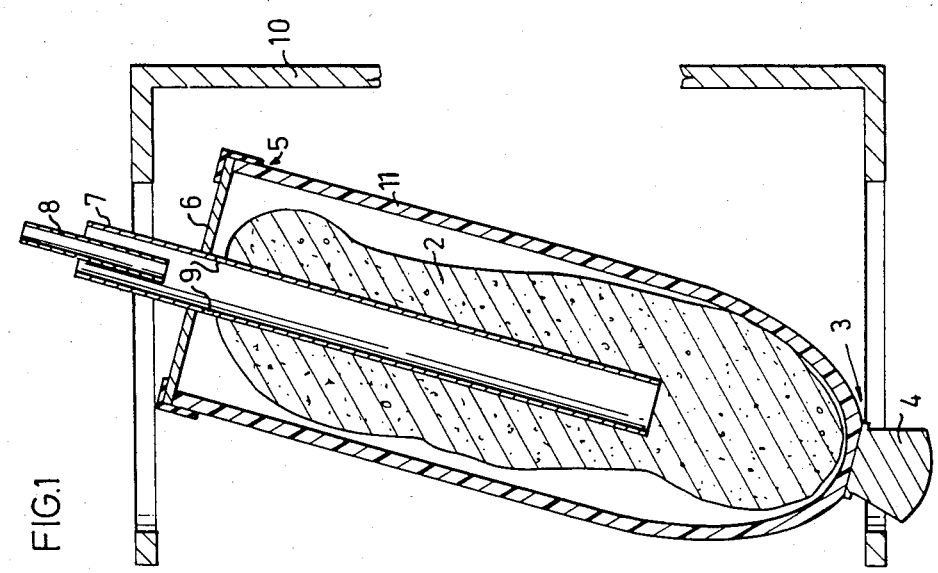
FIG. 2 is a corresponding view in section after shaping the prosthesis cuff to the positive cast.

FIGS. 1 and 2 show the steps of forming prosthesis cuff around a positive cast, in this case a plaster positive cast 2, comprising an extremely accurate reproduction of the actual amputation stump to be received by the prosthesis cuff. In FIG. 1 the cuff is still in the form of a rough cuff 11 which does not conform to the contour of cast 2. In FIG. 2 the cuff has assumed the final shape of prosthesis cuff 1. Both rough cuff 11 and prosthesis cuff 1 are tubularly shaped and have a closed end 3 and an open end 5. Prosthesis cuff 1 has at its closed end 3 an adapter 4. The open end is covered, during the shrinking process, by a lid 6. The adapter 4 may have a retaining formation, (not shown), embedded in the plastics material of the cuff or may be formed integrally with the material of the cuff or otherwise secured to the cuff. The plaster positive 2 is provided with a tubular position indicator 7. The prosthesis cuff 1 and the plaster positive 2 are positioned in relation to each other by means of a stand 10.

In making a lower leg prosthesis cuff by the method to be described, the rough cuff 11 is manufactured by means of injection moulding, in a plastics material having a thermoplatic memory, i.e. a material which after deformation will strive to return to its original shape upon being subsequently heated. Adapter 4 for connection of the lower-leg prosthesis part is preferably embedded in the lower, closed end 3 of the rough cuff 1 at the same time as the injection moulding takes place. The product of the injection moulding has a diameter which is less than that of the final prosthesis cuff 1, and this product is then expanded by at least 25% and preferably by 150% of its original diameter, to form rough prosthesis cuff 11 dimensioned to hold with clearance a typical plaster positive 2 of a leg amputation stump.

Plaster positive 2 is a positive cast of an actual amputation stump and is manufactured in a manner known per se and is provided with the position indicator 7 protruding from that end of the positive cast which is opposite the end which corresponds with the free end of the amputation stump. This position indicator 7 is inserted during production of the plaster positive 2 to mark the most suitable position, from the aspect of placing weight on the finished prosthesis, of the connection point for the lower-leg prosthesis part.

The plaster positive 2 is introduced through the open end 5 of the rough prosthesis cuff 11 and the adapter 4 embedded in the closed end 3 of the rough prosthesis cuff and protruding therefrom is positioned in an outer stand 10 at least partially surrounding the rough prosthesis cuff. In the upper part of this stand, the position indicator 7 protruding from the plaster positive 2 is positioned to be aligned with said adapter 4.

The upper end 5 of the rough prosthesis cuff 11 is then sealed by means of a lid 6, a plate or the like, which may also be formed by the upper part of said stand 10. The position indicator 7 extends through said lid 6 and an inner tube 8 is arranged in the upper end of the position indicator 7, the inner tube 8 communicating at one end with the interior of the prosthesis cuff 1 via one or more apertures 8 and being connected at the other end with a vacuum pump or the like (not shown).

The rough prosthesis cuff 11 with the positioned plaster positive 2 is subjected to heat and, after reaching the shrinkage temperature of the plastic material, the rough prosthesis cuff 11 is forcibly shaped around the plaster positive 2, substantially adapting to its outer contour. Toward the end of the shrinking process a partial vacuum is generated in the space between the outer surface of the plaster positive 2 and the inner surface of the rough cuff 11, by applying suction to the inner tube 8 so that a precise fit of the cuff to the positive 2 is achieved by vacuum forming.

Prior to introduction of the positive 2 into the prosthesis cuff, the plaster positive 2 is preferably provided with a thin, flexible plastics coating.

The invention is not limited to the example described with reference to the accompanying drawings, but can be varied in many ways within the scope of the following claims.

For instance, the vacuum connection to the space between the plaster positive and the outer cuff may be arranged via a separate inlet in the lid 6. Furthermore the lid 6 may be secured to the open end of the rough cuff 11 by means of clamps or similar detachable securing members.

Obviously materials other than plaster can be used to make the positive cast.

In the method described above with reference to the drawings, the heat shrinkage of the prefabricated rough cuff 11 is of subordinate significance and is used in principle only to obtain the most suitable dimensioning of the cuff, i.e. the most suitable dimensioning for the following vacuum shaping. By selecting a suitable shrinkage ratio for rough cuff 11, and by utilizing vacuum-forming for final shaping of the cuff, it is possible to cater for a wide range of sizes of amputation stumps with only a few standard sizes of rough cuff, so that the stocking of such prefabricated rough cuffs can be considerably reduced, as compared with the former practice, i.e. it is no longer necessary to stock a multitude of different cuffs of special dimensions. Thus, as far as rough cuff 11 is concerned, considerable savings can be achieved both from the production and the stocking aspects. Contrary to earlier practice, according to which it was considered that a heat-shrinkable cuff for a heavy patient would require to have a thicker wall than such a cuff for a light patient, a careful analysis of the loads exerted on prosthesis cuffs produced according to the invention, with the cuff positioned in relation to the plaster positive, has surprisingly indicated that the dimensioning requirements to be fulfilled by the cuff are dictated by the load torque occurring upon walking movements, etc. being made. In taking up torque of this type a larger diameter of cuff is advantageous from the design point of view, i.e. the cuff wall can be made thinner if the diameter of the cuff is greater, in order to take up the same load torque. This analysis thus indicates that cuffs of smaller diameter should have thicker walls than cuffs of larger diameter, which is, of course, precisely what tends to happen in any case when standard rough cuffs of predetermined wall thickness are shrunk to the respective diameters required. Design considerations resulting from this analysis in conjunction with the other advantages of the invention make it possible to use a few standard cuffs to cater for all variations in prosthesis stumps since the process of shrinkage and vacuumshaping is now working in the right direction for dimensioning prosthesis cuffs.

I claim:

1. A method of manufacturing a prosthesis cuff to receive an amputation stump, comprising the steps of:
   providing a positive cast of an amputation stump;
   forming a tubularly-shaped rough prosthesis cuff by introducing a starting plastic material having thermal plastic memory into a mold, the mold having an internal shape to form the rough prosthesis with a closed end and an open end, the rough cuff defining an interior space which is smaller than the positive cast;
   embedding an adaptor at the closed end of the rough cuff during formation of the rough cuff, the adaptor being suitable for connecting the rough cuff to another prosthesis part;
   stretching the rough cuff to enlarge the interior space thereof sufficiently to enable the positive cast to fit in the rough cuff;
   inserting and positioning the positive cast in the rough cuff;
   heating the rough cuff, while the positive cast is positioned therein, in a manner that is effective for causing the rough cuff to shrink around the positive cast and to conform to the surface contour of the positive cast whereby the rough cuff is transformed into a finished prosthesis cuff; and
   allowing the finished prosthesis cuff to cool and removing the positive cast from the finished prosthesis cuff.

2. The method of claim 1, including providing a position indicator for marking the most suitable position, from the aspect of the weight to be placed on the finished prosthesis, of the connection point for the prosthesis in the finished cuff, the position indicator being effective to enable alignment of the positive cast relative to the rough prosthesis.

3. The method of claim 2, wherein the position indicator comprises an elongated rod which is partially embedded in the positive cast and which extends along a straight line therefrom and, further comprising the step of aligning the position indicator of the positive cast such that when the cast is inserted and positioned in the rough cuff, the straight line is linearly aligned with a longitudinal direction defined in the adapter.

4. The method of claim 3, wherein the adapter provided at the closed end of the rough cuff protrudes therefrom and the position indicator projects from the open end of the rough cuff when the positive cast is inserted and positioned in the rough cuff, wherein an outer stand is provided at least partially surrounding the rough cuff, and wherein said adapter is positioned prior to the shrinking process in said outer stand said stand having a further portion which is used to position the position indicator protruding from the cast.

5. The method of claim 4, wherein the open end of the rough cuff is sealed by a portion of said stand.

6. The method of claim 2, wherein said position indicator comprises a tubular member protruding from that end of the cast which is opposite to the end corresponding with the free end of the amputation stump.

7. The method of claim 1, wherein said positive cast is formed as a plaster cast and wherein the plaster cast is provided with a thin plastic covering prior to insertion in the rough cuff.

8. The method of claim 1 which further comprises the step of providing a vacuum in the space between the outer surface of the cast and the inner surface of the rough cuff for carrying a final adjustment of the conformance of the rough cuff to the surface contour of the positive cast.

9. The method of claim 1 in which the rough cuff is expanded by at least 25% in the expanding step.

10. A method of manufacturing a prosthesis cuff to receive an amputation stump, comprising the steps of:
    providing a positive cast of an amputation stump;
    forming a tubularly-shaped rough prosthesis cuff by introducing a starting plastic material having thermal plastic memory into a mold, the mold having an internal shape to form the rough prosthesis to include a closed end and an open end, the rough cuff defining an interior space which is smaller than the positive cast;
    embedding an adaptor at the closed end of the rough cuff during formation of the rough cuff, the adaptor being suitable for connecting the rough cuff to another prosthesis part;
    providing a position indicator on the positive cast, the position indicator extending out of the positive cast and being suitable for aligning the cast relative to the rough cuff;
    inserting and positioning said positive cast in said rough cuff;
    heating the rough cuff while the positive cast is positioned therein in a manner that is effective for causing the rough cuff to shrink around the positive cast and to conform to the surface contour of the cast whereby the rough cuff is transformed into a finished prosthesis cuff; and
    allowing the finished prosthesis cuff to cool and removing the positive cast from the prosthesis cuff.

11. The method of claim 10, further including the step of embedding, during the molding of the rough prosthesis, an adapter at the closed end of the rough cuff, the adapter being suitable for connecting the rough cuff to another prosthesis part and further comprising the step of aligning the position indicator of the positive cast to the adapter such that when the cast is inserted and positioned in the rough cuff the position indicator and the adapter are brought into alignment with one another.

12. The method of claim 11, wherein the adapter provided at the closed end of the rough cuff protrudes therefrom, wherein the position indicator projects from the open end of the rough cuff when the positive cast is inserted and positioned in the rough cuff, wherein an outer stand is provided at least partially surrounding the rough cuff, and wherein said adapter is positioned prior to the shrinking process in said outer stand, said stand having a further portion which is used to position the position indicator protruding from the cast.

13. The method of claim 12, wherein the open end of the rough cuff is sealed by a portion of said stand.

14. The method of claim 10, wherein said position indicator comprises a tubular member protruding from that end of the cast which is opposite to the end corresponding with the free end of the amputation stump.

15. The method of claim 10 which further comprises the step of providing a vacuum in the space between the outer surface of the cast and the inner surface of the rough cuff for carrying a final adjustment of the conformance of the rough cuff to the surface contour of the positive cast.

16. The method of claim 10 in which the rough cuff is expanded by at least 25% in the expanding step.

* * * * *